United States Patent
Herrero

(10) Patent No.: US 6,387,042 B1
(45) Date of Patent: May 14, 2002

(54) APPARATUS AIDING PHYSIOLOGIC SYSTOLIC AND DIASTOLIC DYNAMICS OF CARDIAC CAVITIES

(76) Inventor: Juan Hernandez Herrero, c/ Los Caballeros, 16, 80834 Barcelona (ES)

( * ) Notice: Subject to any disclaimer, the term of this patent is extended or adjusted under 35 U.S.C. 154(b) by 0 days.

(21) Appl. No.: 09/513,813

(22) Filed: Feb. 25, 2000

Related U.S. Application Data

(63) Continuation-in-part of application No. PCT/ES99/00274, filed on Aug. 23, 1999.

(51) Int. Cl.[7] .......................... A61F 13/00; A61N 1/362
(52) U.S. Cl. ............................. 600/37; 600/16
(58) Field of Search ................. 600/37, 16–17; 623/3; 601/153

(56) References Cited

U.S. PATENT DOCUMENTS

| | | |
|---|---|---|
| 3,827,426 A | 8/1974 | Page et al. |
| 4,192,293 A | 3/1980 | Asrican |
| 4,448,190 A | 5/1984 | Freeman |
| 5,131,905 A | 7/1992 | Grooters .................... 600/16 |
| 5,383,840 A | 1/1995 | Heilman et al. ............ 600/17 |

*Primary Examiner*—John P. Lacyk
(74) *Attorney, Agent, or Firm*—David L. Garrison; Garrison & Assoc. PS

(57) ABSTRACT

Apparatus aiding physiologic systolic and diastolic dynamics of heart cavities designed to assist the systolic contraction of the heart ventricles, and to simultaneously or alternatively regulating the diastolic relaxation, provoking an atrial contraction, the ventricular mode comprising a stiff conical wrapping (12) surrounding the ventricles (11, 11*a*) fastened to a first ring (13) located on the base of the ventricles and with a distal tip (14) close to the cardiac apex, and a second internal concentrical ring (18) attached to the mouth of a conical bag (19) fastened through a distal vertex (19*b*) to said tip (14), so that the second ring (18) when rotating provoking in a first course a narrowing of the bag (19) squeezing the ventricles, aiding to the ventricular systole, and in a reverse turn allowing the diastolic filling regulating the ventricular diastole, and the atrial mode comprising a cap (20) surrounding the atria (21, 21*a*) leading them toward the ventricles (11, 11*a*) by tension members and wheels associated to the wrapping (12) provoking the atrial systole.

16 Claims, 3 Drawing Sheets

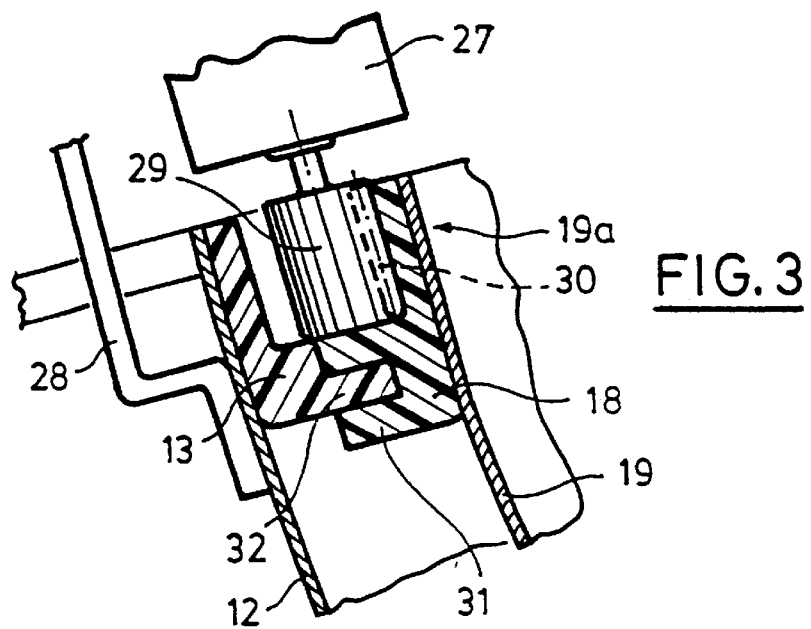
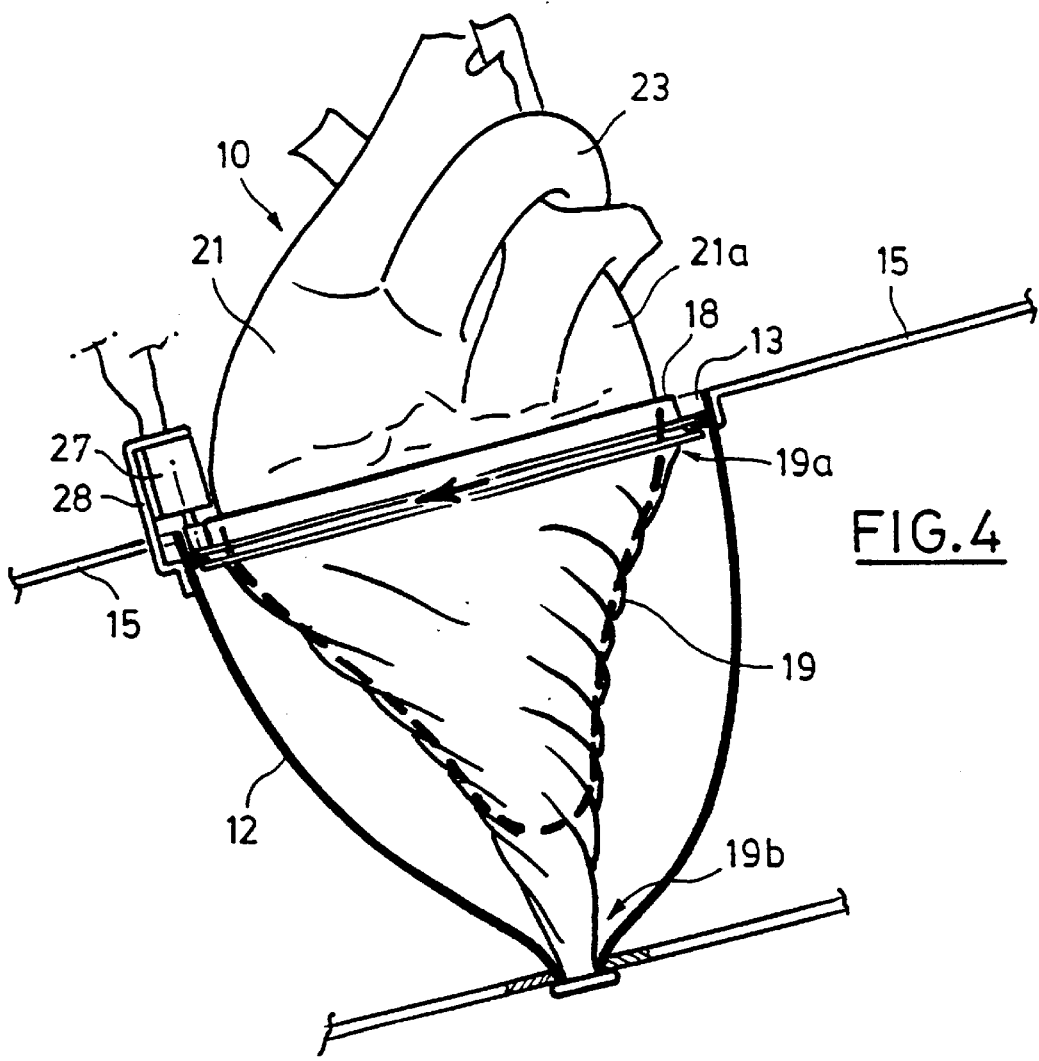

APPARATUS AIDING PHYSIOLOGIC SYSTOLIC AND DIASTOLIC DYNAMICS OF CARDIAC CAVITIES

This is a continuation-in-part of co-pending International Application PCT/ES/99/00274 with priority of PCT/ES98/00238 filed on Aug. 28, 1998 designating the United States.

FIELD OF THE INVENTION

This invention relates to an apparatus devised to aid the heart in its contractile function.

The object of the invention consists in an apparatus to treat cardiac insufficiency through a system similar to the physiologic way, improving heart emptying, allowing to initially and, in further controls, regulate contractility and distention parameters as well as cavity filling and emptying times fitting the mechanics to the heart electric activity and keeping a physiologic way because the apparatus aids the heart in its own operation working in a similar way to the systolic contraction of the physiologic ventricular and atrial musculature.

The apparatus of the invention allows to improve the contraction of heart cavities in global dilatations (in the typical case of dilated cardiomyopathy) as well as the contraction of segmentary dilatations, so also asynergies, dyssynergies, aneurysms and zonal dilatations of many cardiopathies can be prevented.

BACKGROUND OF THE INVENTION

Cardiac insufficiency in its concept of incapacity for the heart to meet its blood pumping function is a frequent state to which one can be lead by several causes and mechanisms.

It is the cause of physical impairment, functional incapacity and a situation of illness in many thousands of persons, and it is the mechanism which leads a great number of patients to death.

Many attempts have been made to try to overcome or to relieve cardiac insufficiency, and during last years, the advances are considerably great because of the always better knowledge of the heart physiologic and pathologic mechanisms as well as those of the rest of the organs and systems which are involved in its operation, as well as the progress of diagnostic and therapeutic techniques in their pharmacologic, mechanic and electric features.

All of it leads to an important advance in the treatment of cardiopathies with subsequent improvement of survival, quality of life and in the relief or disappearance of the symptoms and complications to which cardiac patients are exposed.

However, the field in which advances have still to be made is very large. The evolution of the cardiac insufficiency is attenuated with drugs and final failure is significantly delayed compared with former times, but still we are not capable to prevent it nor to provide the myocardium with the lost strength when it reaches a certain degree of dilatation and diminution of its contractile capacity.

It is so to such extent that, during last decades a number of heart transplantation units have been developed to provide with a new heart from somebody else patients whose prognosis was unfortunate because the rest of the medical possibilities were exhausted to stop the evolution towards definite failure in a weakened heart.

Artificial hearts have been also developed which include a pumping system in the apparatus itself. But said artificial hearts, because of the haemolysis they produce and other important medical drawbacks and high economic costs, up to now, are not long lasting and in many cases they are applied temporarily while the patient is waiting for a heart transplantation.

The Revista Española de Cardiología, vol. 51, pages 23–30, July 1998, publishes an article by Dr. Francisco Torrent Guasp, where a contention prosthesis is disclosed which consists in a stiff or malleable non extensile ring which carries out a contention task in the ventricle two basal thirds, narrowing the ventricular mass. Said contention prosthesis would limit a further heart dilatation but would not allow to regulate the diastolic volume nor would make further modifications possible and it wouldn't improve systolic emptying. Said article includes a description and illustration of the ventricular mechanics in the function of which four main ventricle motions are distinguished: narrowing, shortening, lengthening and enlarging (FIG. 3, page 522).

Patent U.S. Pat. No. 5,383,840 discloses a biocompatible device for ventricular aid and arrhythmia control including a compressing assembly which comprises a band for wrapping the heart perimeter and means to more or less closely fit the band around the external walls of the ventricular cavities during predetermined periods of time so that a pressure is applied to said ventricles which is approx. transversal to the lengthwise axis thereof, of an adjustable value, in synchronism with the systolic cycles of said cardiac cavities, in addition to the cavity walls narrowing-shortening and said means allowing further loosening and dilatation of said walls chronologically with the cardiac cycle.

Said patent discloses in details other systems of the state of the art applied to same aim among which the patent U.S. Pat. No. 4,304,225 is referred to which also discloses a pressure band.

Other documents of the state of the art relative to the object of this invention are disclosed in patent U.S. Pat. No. 4,448,190 which includes a wrapping associated to pumping means to closely fit or loosen an organ such as the aorta or the ventricles while a series of electrical impulses are sent in synchronism. Another similar device appears disclosed in patent U.S. Pat. No. 5,131,905.

In all these backgrounds the devices compress the heart transversally, as if a manual massage was performed. This way of compressing, in spite of being effective, is different of the physiologic behaviour in the systolic contraction of the ventricular muscle, which expels the blood from the apex to the base of the ventricles.

On the other hand, none of mentioned backgrounds foresees means for applying a contractile treatment similar to that of the atria and to allow treating simultaneously or separately atria and ventricles.

DESCRIPTION OF THE INVENTION

Unlike mentioned backgrounds, the invention proposes an apparatus aiding physiologic systolic and diastolic dynamics of the heart cavities which we will call SPES (system for pressing electrosyncronically) for aiding the heart in its contractile function.

The apparatus consists in a stable structure or wrapping, acting as a receptacle, having a contour similar to that of the ventricles, approximately cone-shaped, and which surrounds/sheathes them, the mouthpiece of which includes a first stiff ring which the same as a distal tip of the structure, distal from the ring and on which the heart apex will be arranged, is fixed to the body skeleton (ribs) for example with flexible tension members or semi-stiff members having the suitable texture which guarantee its relative locking.

Coupled to said first stiff ring, there exists a second stiff ring, having a slightly smaller diameter, guided with possibility to concentrically revolvingly slide, a driving device having been provided fixed to the external ring and with a toothed member geared with a peripheral toothed profile of the external wall of the internal ring, so that when said motor acts the internal ring is revolvingly moved, sliding driven on the external ring which remains fixed.

An approximately cone-shaped bag of flexible fabric, similar to the ventricular contour is connected by its mouthpiece to the rotating internal ring, above described, and its vertex is internally joined to the distal tip of the external stiff wrapping.

By means of said arrangement, said flexible internal bag remains in contact with the pericardium which wraps the ventricles, containing the heart within it and in turn surrounded by said stiff structure integral with the external ring in such a way that the apparatus squeezes the internal bag when the internal ring rotates.

That is to say, the behaviour of the apparatus which is proposed acts according to the heart physiology of systolic contraction of the ventricular musculature, carrying out an emptying upward the aortic and pulmonary valves, which results particularly effective for systolic emptying as emptying direction is the same as that of the myocardium at the systole.

The structure, surface and distribution of said bag fibres will be selected so that they allow to apply different pressures on one or the other ventricle.

The apparatus includes in addition:

control means to remote monitoring, during the operating periods, the application of rotations in one or the other direction of the internal ring, in synchronism with the physiologic cardiac dynamics which comprise:

a driving system;

a battery or power supply for the driving system;

a regulating system; and means to keep the external ring and the distal tip of the stiff structure distal thereof fastened on the thorax so that said structure is arranged around the heart in such a way it cannot be taken away.

According to a preferred embodiment of the invention, the apparatus includes a cap which is placed on the atria adapting itself to their contour and having care of the incuts of the caval and pulmonary veins which converge on them. This cap is joined by means of tension members which have a toothed profile sector and which are geared in a controlled way with driving toothed wheels located on the external face of the stable/stiff structure which wraps the ventricles or in the external ring.

The anatomy of the atria and their topographic relation with the large vessels do not allow to so easily closely fit them by means of a bag or sheath similar to the one proposed for the ventricles, therefore the atrial system will consist in a cap surrounding them.

Said cap must have a shape which can be adapted to the atrial external surface, with the suitable incuts at the area joining them to the vessels so that these latter are not compressed when constricting the atria.

This cap can be narrowed and lead downward in craniocaudal direction by means of tension members having a toothed profile associated to driving toothed wheels which are supported on the apparatus external wrapping or external ring.

The rotation of said wheels will make the atrial cap go downwards the ventricles, compressing the atria and obliging them to empty themselves and to provoke atrial emptying through the mitral and tricuspid valves or to go up and decompressing them, allow the atrial diastole.

If the system is only an atrial system, a protecting sheath will wrap the ventricles with the aim of preventing the friction produced by the tension members and of providing a support for the driving system.

If the system is double, i.e. atrial and ventricular, the tension members of the atrial module and its closing mechanism will be external with respect to the ventricular module (external stable structure) to also prevent that its motion damage the heart surface.

The apparatus can be arranged surrounding only the ventricular part with which only the ventricular diastole and systole will be controlled.

It can be also arranged around the atria controlling atrial diastole and systole.

When wished, both systems will be matched although it has to be quite clear that the wrapping parts are specific for one and the other cavities, the atrial systole, the atrial diastole, the ventricular systole and the ventricular diastole being in said case regulated in a sequence identical to that of the heart cycle physiology.

A significant advantage of the apparatus proposed is that it is placed on the external surface of the heart. Thus it does not contact the intracavitary blood so it does not damage the blood cells as do present artificial hearts above mentioned and unlike the alternative systems of cardiac aid disclosed in mentioned patents, it provokes a physiologic action and makes an application on the atria possible, independent from or combined with the treatment of the ventricles.

Operating mechanisms: A) Ventricular mode

Coinciding with the ventricular systole, the internal ring, base of the flexible bag, rotates around its center, driven by the driving system. As the internal cone vertex remains fixed on the external structure and therefore cannot move, when its base rotates, the walls are constrained and oblige the ventricles, contained within them, to empty themselves, doing it in same way as the heart is physiologically emptied. The blood contained within them will be emptied toward the cone base which is the place where the sigmoid valves (aortic and pulmonary) are located and will be poured toward the great vessels (aorta and pulmonary artery).

The more degrees the internal ring rotates, the greater will be the cone narrowing, lower the volume contained and larger the amount of blood expelled in the systole of the ventricles toward the great vessels, i.e., more are we increasing the so-called "ventricular ejection fraction".

Time wished for each period of constriction to achieve a suitable emptying will be determined for each case.

Once the systole period ends, the ventricles must relax to be able to be filled in the diastole.

When rotation occurs in the opposite direction to the above mentioned, the flexible fabric bag which wraps the ventricles comes back to its former shape, recovers the capacity, larger when the ring is rotating more around it in its return, and allows that the ventricles, contained within it, relax in diastole, and are filled with the blood coming from the atria.

To this aim, at the scheduled moment, the internal ring is caused to rotate in the opposite direction to the former and wished diastolic volume will be achieved. If it is wished to recover the maximum possible diastolic volume, the return will be total, coming back to the position in which the internal cone has its maximum volume.

If in a patient it is wished to diminish the diastolic filling, the return will be adjusted so that the internal ring rotates less degrees preventing thus an excessive diastole filling.

The possibility to adjust the amount of ring return up to its primary position likewise offers the capacity to determine which will be the maximum ventricular relax we wish to allow and therefore to adjust the diastolic volume according to our wish.

This allows in addition to reduce or eliminate the excessive heart distension, that means, the diastolic congestion, which is a very important factor in cardiac insufficiency when the ventricles have exceeded a critical degree of dilatation.

Also the time it is wished for each period of relax will be determined to achieve a suitable filling in each case.

Thus the possibility to adjust the rotation in one direction or the other leads to regulate with it at our will the systolic volume and the diastolic volume and to fight so the two main components of cardiac insufficiency: insufficient contractility and excessive dilatation.

B) Atrial mode

In many cases, the patients are in atrial fibrillation. Up to now, the single medical actions for this situation consist in:
1) trying to recover the sinus rhythm with drugs or electrical cardioversion
2) controlling with drugs the ventricular frequency of a permanent fibrillation
3) some times, to carry out the ablation of the atrio ventricular conduction when ventricular response cannot be controlled.

In other cases, although the patient is in sinus rhythm, there are atrial dilatations which would take profit of a mechanical aid for their emptying.

With the system we propose, it can be tried to squeeze the atria in a way similar to the atrial systole which, in cardiac cycle, coincides with the last part of the ventricular diastole.

This means three important advantages:
1) it is taken profit of the percentage in which the atrial contraction contributes to cardiac output;
2) atrial dilatation is prevented;
3) as its emptying is kept it is prevented that blood clots are formed within it, with subsequent risk of pulmonary or systemic embolisms.

If the patient has a sinus rhythm of his/her own and it is wished to aid the atrial systole, when the P wave of the electrocardiogram appears a rotation will be provided of one toothed wheel which has to pull down the cap wrapping the atria.

This rotation can generate in said cap a displacement parallel to the larger heart axis, so they would be only moved downward. But if it is wished, providing the tension members which fasten said cap with a determined inclination on said larger axis, it would be achieved that when the toothed wheel rotates, a certain degree of twist occurs, having always care that the twist is not such that it chokes the atrial great vein entrances.

Implantation and Fastening

Initially and while the system technical evolution does not allow another procedure, placing will occur with a surgical operation with thoracotomy.

The apparatus wrapping the heart will be placed outside the pericardium. Bearing in mind that the heart and the anatomic tissues which surround it (lungs, great vessels and all the mediastinal structures) frailty prevent that they are surgically fixed on them, said apparatus must be fixed on stronger nearby structures, the anatomy and function of which will not be damaged with the proper motion of the apparatus. As it was mentioned, the external ring and the external wrapping tip are fixed on the ribs to prevent apparatus twists and displacements and at same time to provide stability and support for the system operation.

In the surgical act of implantation, the other end of each tension member of flexible material will be fixed on itself surrounding a rib at the best suited point nearby, so that it does not damage nervous or vascular structures.

It will be convenient that several tension members fasten the apparatus external ring and that one or several fasten the distal vertex.

The number of tension members will be sufficient to have the apparatus tightly fastened on the chest. Their width will be suitable in order the motion does not damage the ribs on which they have to be fastened. The length will be according to the sizes of the apparatus and, last, in the surgical act, the surgeon will determine which length of each tension member has to be bent on itself and be stitched with suture in order it offers suitable stability without distorting the anatomy of the region by provoking unsuitable angles. Alternatively to the tension members, one or more semi-stiff members having suitable profile may be used.

In order the heart remains fastened within the apparatus, tension-memberlike girths having a system similar to that of the suspender of a trouser, can be passed over the heart, leaving it wrapped and, by means of a closing system, which can be with surgical stitches or otherwise, be fastened on the apparatus itself, and so prevent that the apparatus is displaced or the heart goes out of it.

The system has the advantage that the apparatus can be easily withdrawn later on in the event the same patient has to suffer a surgical operation on the heart, for example, to make an aorto-coronary by-pass or for the possible case that any circumstance makes advisable to renew the apparatus.

Power supply and conduction system

The ideal power supply system will be a large capacity battery type generator which allows to implant it within the organism of the patient, periodically renewable, as it is done nowadays with the pace-maker generators. This will have the advantage not to depend on an external power supply which requires a connection between outside and inside the organism.

If in principle power requirements do not allow that the battery is internal, a transthoracic cable may connect the apparatus motor to the power supply which can be external batteries the patient bears in an haversack as presently do those bearing an artificial heart.

Chronological regulation with relation to the electric cycle of the control system An electronic generator, similar to that of a pace-maker and which will be implanted within the organism of the patient in same surgical act, will be the one that will send to the driving system the impulses to start the contraction and distension.

Also from it will be determined:
a) the moment of starting the contraction
b) the duration of the contraction
c) the amount, speed and duration of the rotation of the ring for the contraction
d) the moment when the distension begins
e) the duration of the distension
f) the amount, speed and duration of the rotation of the ring for the distension.

To keep a suitable sequence in the contraction of the cardiac cavities and to keep the physiologic periods of filling and emptying, it is required to adjust the mechanical activity to the electrical activities of the heart, respecting the periods of isovolumetric contraction, emptying, isovolumetric relaxation and filling.

A sensor similar to the cable of a pace-maker will detect the beginning of QRS ventricular complex of the electrocardiogram in order that, same as for the physiological ventricular systole, it is it that determines the beginning of the constriction and assist to ventricle systolic emptying when it is sought to start the ventricular module.

The same sensor or another similar will have to detect the P wave of the electrocardiogram when the atrial module is to be used.

If the ventricles are stimulated by a pace-maker, the ventricular spicule will be the detonative of the beginning of the start of the rotation for the ventricular systole.

If it is an atrial mode and the patient has no atrial rhythm of his/her own with detectable P wave, a pace-maker in atrial or bicameral mode will be which will awake the atrial mode from the spicule of the atrial cable.

Regulation in further controls

Just as it can be done with a pace-maker, these parameters may be controlled and readjusted from outside as many times as it is wished to obtain an optimum performance in each patient.

Clinical and radiological controls and more accurately echocardiographic controls will show the state of each patient and the adjustments to perform each time.

Driving mechanism

An adjustable rotor will be the driving element of the ventricular contraction system. The rotor connected to the battery and to the regulation system will do that the internal ring rotates during the systole as many degrees as it is scheduled in order to achieve the wished systolic expression and to aid the ventricles to be emptied.

The rotation in opposite direction of this rotor will do that the cone delimited by the internal bag increases the capacity in the diastole in order that the ventricles are filled in the amount scheduled to obtain a best hemodynamic performance.

The motor may be fixed to the apparatus external ring which will keep it stable with relation to the heart. The very best location on said ring or wrapping casing will be depending on the occupied spaces, trying that its opacity does not interfere in further scanning in echocardiographic controls which have to be carried out for patient follow-up and suitability of the apparatus operating parameters.

As the external wrapping (external ring and distal tip of the wrapping) have been fixed on the chest by means of the tension members above mentioned in the fastening system, the apparatus and the motor will remain thus stable on the thorax and suitably wrapping the heart.

They can be arranged surrounding only the ventricular part so that only the ventricular systole and diastole will be controlled.

Also a cap can be applied around the atria controlling the atrial systole and diastole.

In the events when it is wished, both system will be matched and synchronizing the mechanisms the atrial systole, the atrial diastole, the ventricular systole and the ventricular diastole will be regulated in identical sequence to that of cardiac cycle physiology.

An explanation of the apparatus of the invention is given below on the ground of the examples of embodiment thereof which are illustrated in drawings attached which have to be taken as illustration and not a limitation to the scope of the invention.

SHORT DESCRIPTION OF THE DRAWINGS

In said drawings:

FIG. 3 is a view of a detail at larger scale of the coupling between the driving gear and a peripheral toothed section on the external face of the internal ring;

Figure 1:
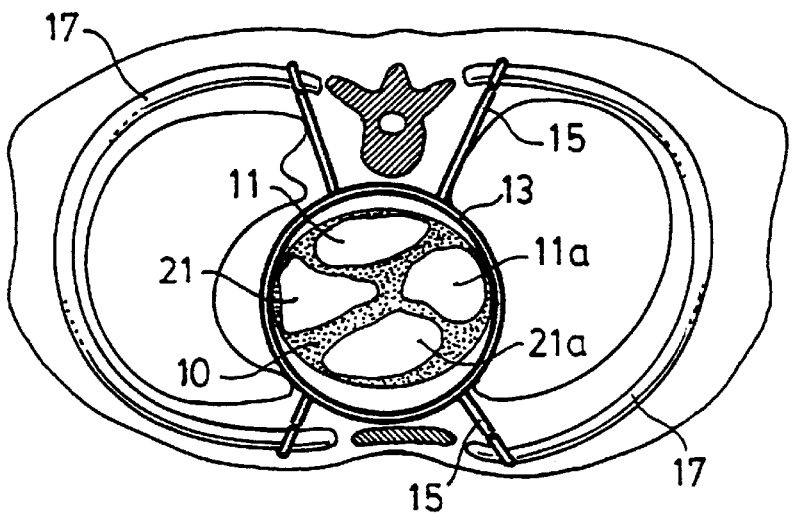
FIG. 1 illustrates a cross section view of the heart which schematically shows the assembly of the two rings which surround it and the tension members or fastening bands of the external ring, fixed on the patient ribs.
Figure 2:
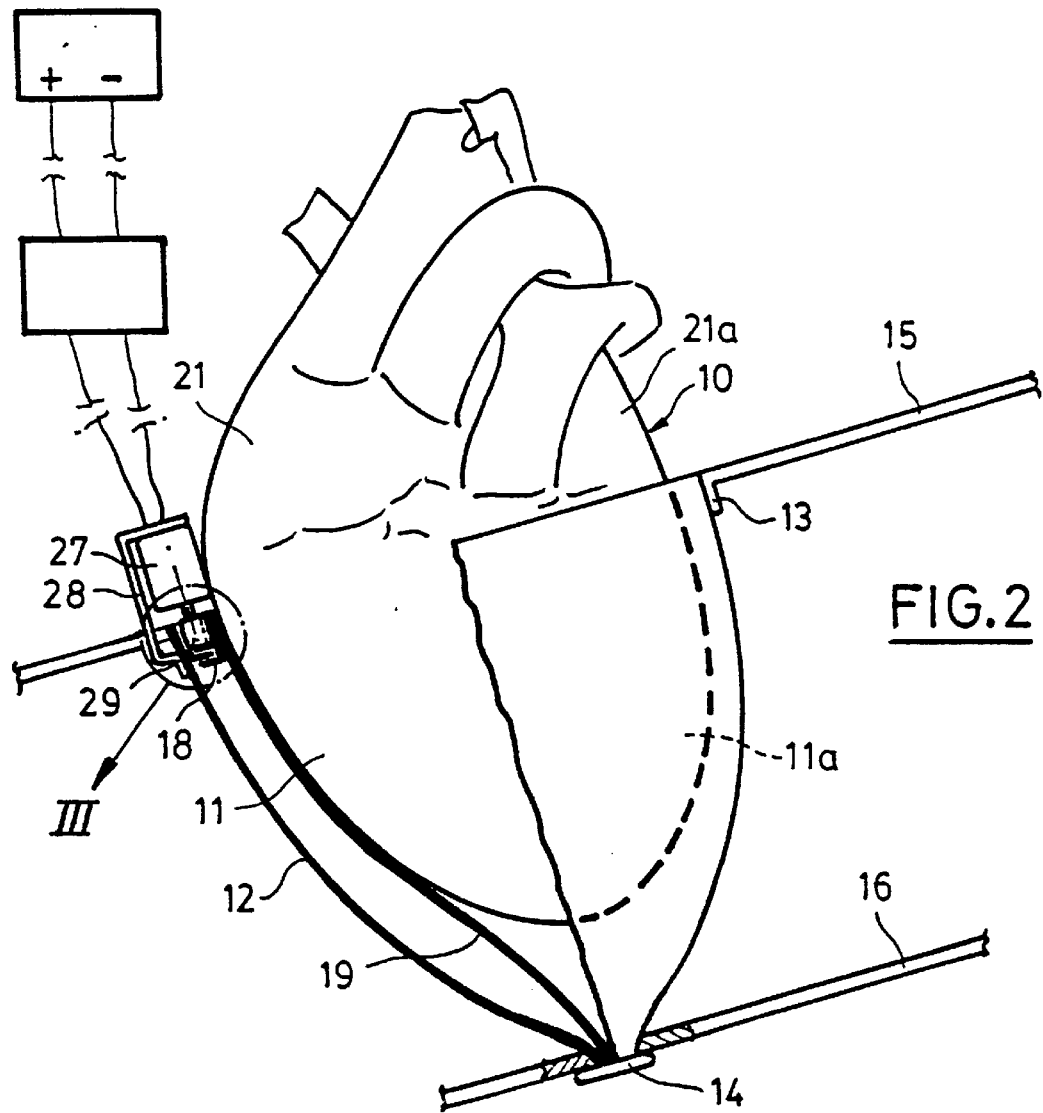
FIG. 2 shows a lengthwise section of the heart in which it can be seen the assembly of the parts forming the apparatus and namely the external wrapping structure and the internal flexible fabric bag as well as the motor assembly which is applied on said internal ring.
Figure 5:
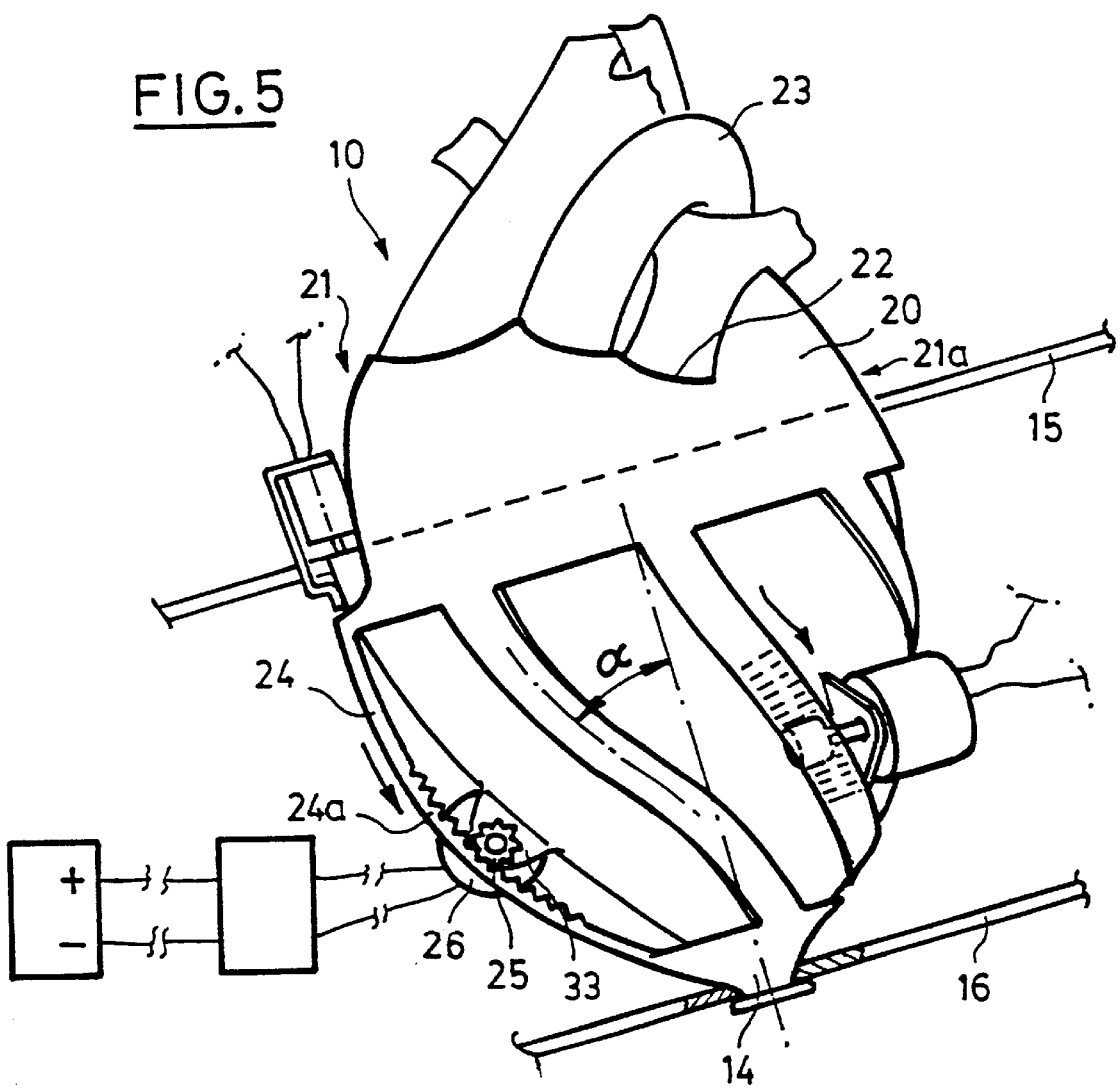
Figure 6:
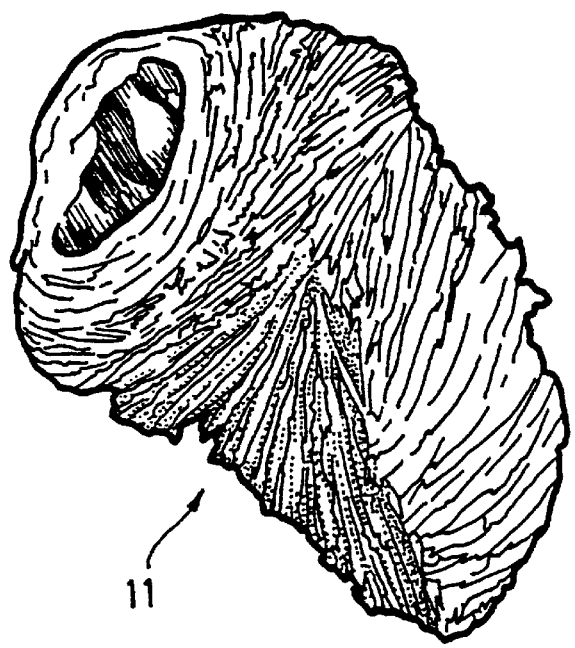

FIG. 4 illustrates a view equivalent to that of FIG. 2 but with the flexible internal bag twisted and therefore acting so that it squeezes the ventricles, corresponding to the maximum rotation of the internal ring in this direction; the rotation in the opposite direction returns the bag to the situation of FIG. 2 and the ventricles to a relaxed situation; and FIG. 5 is an external view of the heart with an embodiment of the apparatus applied to the atrial portion or ventricular and atrial portion; and FIG. 6 shows in perspective the helicoidal distribution of the ventricular myocardic fibres according to an illustration which appears in the work Cardiac Anatomy, by Robert H. Anderson and Anton E. Becker Gower Medical Publishing London, 1980.

DETAILED EXPLANATION OF SOME EXAMPLES OF EMBODIMENT

According to said figures, the apparatus aiding in the physiologic systolic and diastolic dynamics of the cardiac cavities this invention proposes comprises:

a wrapping (12) as a receptacle having a contour similar to that of the ventricles (11, 11a) which it surrounds, the mouthpiece of which is attached to a first stiff ring (13) and with a distal tip (14) on which the heart apex (10) will be arranged, both said first stiff ring (13) and said tip (14) being fixed on the body skeleton of the patient;

a second stiff ring (18) having a slightly smaller diameter, coupled to said first stiff ring (13) which surrounds it, with possibility of revolvingly sliding, supported, guided on said first ring (13) and a displacement concentrically to it;

a bag (19) of flexible fabric, similar to the ventricular contour, joined by a mouthpart (19a) to said second stiff ring (18) and the vertex of which (19b) or bottom of said bag (19) is internally joined to the tip (14) of the external wrapping (12);

means for applying to said second stiff ring (18) during predetermined periods of time, rotations to the right and to the left, having an adjustable amplitude, in synchronism with the ventricular (11, 11a) systolic and diastolic cycles determining a twist of the bag (19) which provokes a squeezing of the ventricles (11, 11a) contained within it aiding thus to systolic emptying and later on to rotating the ring (18) in opposite direction, a relaxation which allow the diastolic filling; and control means for remote monitoring the application during the operating periods of said rotations in synchronism with the physiologic cardiac dynamics.

The wrapping (12) adopts an about conical configuration and it is advantageously stiff and the bag (19) is conical-funnel-shaped.

Said means to apply rotations to the right and to the left to said second stiff ring (18) comprise as it can be seen in FIG. 2 and namely in the enlargement of FIG. 3 a driving member (27) the operation of which determines an alternate succession of spiral twists and expansions of said flexible bag (19) which surrounds the ventricular walls because it is fastened by its vertex (19b) or bottom on the point (14) of the stiff wrapping (12).

As it is detailed in FIG. 3 said driving member (27) is fixed by means of a support (28) to the first external ring (13) and its shaft possesses a pinion (29) which is geared with a peripheral toothed profile (30) defined on the external wall of the second internal ring (18) so that when said motor (27) acts, the ring (18) is displaced in rotation, sliding conducted by a guiding configuration on the ring (13) which remains fixed.

Said guiding configuration is constituted, in the example of embodiment illustrated in FIG. 3 by a protrusion (32) which emerges from an edge of the external ring (13), said protrusion (32) being arranged engaged in a groove of the ring (18) delimited by walls (31).

According to a preferred embodiment of the invention which is illustrated in FIG. 5 the apparatus comprises a specific wrapping determined by the assembly (12, 19) to be applied to the atria (11, 11a) and a wrapping designed to be applied to the atria (21, 21a) if required, so that the apparatus can be simple, only ventricular, only atrial or mixed ventricular and atrial.

Said wrapping applied to the atria (21, 21a) comprises as it can be seen in FIG. 5 a cap-like element (20) adapted to its contour and respecting the incuts (22) of the caval and pulmonary veins (23) in which they converge and means to squeeze said cap (20) and to take it downward the ventricles (11, 11a) approximately in cranio-caudal direction toward the ventricles and thereafter to release it allowing the recover-relax of said atrial cavities (21, 21a).

The means to squeeze said cap (20) and then release it comprise tension members (24) with a toothed profile (24a) associated to driving toothed wheels (25), driven by a motor (26) with supports (28) on the wrapping (12) of the apparatus, the rotation of the wheels (25) driven by the motor (26) will take the atrial cap (20) down to the ventricles (11, 11a) compressing the atria (21, 21a) obliging them to be emptied and provoking the atria emptying through the mitral and tricuspid valves or to take them up and decompressing them allowing the atrial diastole.

Although it has not been show in the drawings it is stated that if the system is only an atrial system, a protecting sheath will wrap the walls of the ventricles (11, 11a) with the object to prevent the friction produced by the tension members (24) and to provide support to the driving system, said cap (20) being related by said tension members (24) to several points of its periphery.

As it was mentioned, the first stiff external ring (13) of the assembly and the point (14) of the stiff wrapping (12) distal from it are fastened on the skeleton of the patient and more concretely on its chest so that said wrapping (12) is arranged around the heart (10) in order it cannot be taken away.

For such purpose, tension members (15, 16) or semistiff members have been provided that relate the first ring (13) as well as the point (14) of the wrapping (12) with the ribs (17) adopting the contour required and said members, adapting themselves to the anatomy of the region pass through the suitable interstices in order to, without damaging nor compressing organic structures, become fixed on the ribs (17) on at least three differentiated ares.

Although they are not detailed in the drawings, ribbons or strips have been provided which surround the heart (10) spreading on said stiff wrapping (12)and keeping it in an operative position and being fixed by the junction to each other of said ribbons or with the external part of the stiff wrapping (12) by stitching or another fixing means.

In the event of a ventricular and atrial mixed system the fastening means of the wrapping or the cap (20) of the atria (21, 21a) will be extended on the wrapping (12) of the ventricles (11, 11a).

Said control means to drive the apparatus will comprise a small-sized electronic generator with an impulse transmitter of a pace-maker type, programmable with possibility to generate two types of differentiated impulses the driving members (26, 27) being a small-sized compact impulse motor with an operating electronic circuit so that according to the type of impulse received it drives in rotation the motor shaft (26, 27) in one or the other direction.

The power supply of said driving member (26, 27) will be a large capacity and long lasting battery which may be implanted in the body of the patient or it will be obtained from outside through a transthoracic cable connecting a motor (26,27) and operating circuit to an external generator and power supply such as external batteries the patient carries in an haversack.

Control means to drive the apparatus comprise a small-sized electronic generator with an impulse transmitter like a pace-maker, which can be scheduled, preferably capable to generate at least two types of differentiated impulses and which will be implanted within the organism of the patient in same surgical act, it will be the one which sends to the driving system (an impulse motor having an operating electronic circuit for rotation in one direction or the other) the impulses to start contraction and distension.

Also from said electronic generator following parameters will be determined:

A) the moment the contraction starts;
B) the duration of the contraction;
C) the intensity of the contraction, i.e., the degree of squeezing which will be determined by the amount of rotation of the ring;
D) the speed of the contraction
E) the moment when the distension starts;
F) the duration of the distension;
G) the amount of the distension, i.e., the maximum diastolic volume which will also be determined by the amount of rotation of the ring;
H) the speed of the distension.

In a way similar with what can be done with the pace-makers, these parameters may be controlled and readjusted from outside as many times as it is wished to obtain an optimum performance in each patient.

Ways of stimulation:

Initially, several possible situations occur as for the way of stimulating the atria, ventricles or all of them, according to the model of support being used and which will be the basic rhythm of the patient and whether he/she is bearing a pace-maker.

1)Patient in sinus rhythm with simple atrial supporting module:

The spontaneous electric activity of the atria corresponding to the ECG P wave will be determinant to the start of the contraction of the atrial module to achieve the active emptying of the atria in the final stage of the ventricular diastole.

2) Patient in sinus rhythm with ventricular supporting module:

The electric activity of the ventricles corresponding to QRS complex of the ECG will be the determinant to start the contraction of the ventricular module to achieve the systolic emptying of the ventricles.

It is necessary to bear in mind the physiologic presphygmic period (also called the period of isovolumetric contraction) which generally shall be maintained between the appearance of the electric activity and the start of the ventricular module shortening.

Initial and further regulations depending on the situation of each patient, will determine how long this period has to be in each case.

3) Patient in sinus rhythm with atrial-ventricular module:

Both systems will be matched, regulating the atria from their electric activity (corresponding to P wave) and the ventricles from theirs (corresponding to QRS complex).

4) Patient in atrial fibrillation with single atrial module:

There exists the possibility that the patient has no detectable atrial electric activity in the form of P wave. The typical and more frequent situation is the atrial fibrillation. In this case, if the decision is made to use the atrial module, it will be solved by means of an atrial pace-maker which, not only will generate a stimulus each period of time wished, but it will be the detonative for having the atrial module contracting the atria from outside. By means of this system, we will not only achieve a rhythmic rhythm but also we will cause the atria contract from outside and thus the three injurious factors of the atrial fibrillation will be solved:

a) the loss of rhythmicity
b) the loss of atrial contractility
c) the dilatation of the atria 5) Patient in atrial fibrillation or flutter with simple ventricular module:

It will be regulated in the same way as for the patient in sinus rhythm from an electric signal of ventricles corresponding to QRS complex.

6) Patient in atrial fibrillation with an atrio-ventricular module:

Equal to the case of the atrial fibrillation with only atrial stimulation, a pace-maker shall have to generate atrial impulses, from which the atrial module contraction will start.

After some milliseconds lapses (the physiologic ranges from 120 to 200) which is the time required for the atrio-ventricular electric transmission, and so that it can also be regulated for each patient, the ventricular module will be started maintaining thus the atrio-ventricular mechanical sequence.

7) Patients bearing pace-makers:

If the patient bears a pace-maker, the sensor will detect the atrial, ventricular spicule or both of them, depending on which is the stimulation mode, to make atrial and/or ventricular systoles fit to them.

If the patient is in atrial fibrillation and it is wished to use the atrial contraction mode, a pace-maker will act generating an atrial artificial electric stimulus which will be detected by the system, and the atrial mechanics will adjust itself to it as if it was a physiological P wave.

The ventricular module will be adjusted so that the twist of the flexible bag starts a moment after QRS complex appears to meet the physiologic period of isovolumetric ventricular contraction. This period has to be initially regulated and, in further controls, from outside.

The moment when ventricular bag rotation and twist is to be started to contribute to the ventricle systole is determined, as for the heart physiologic behaviour, by the moment when the ventricular electric activity appears and ECG QRS complex is generated. For this, a sensor like to the ventricular pace-maker probe determines the appearance of the ventricular electric activity either spontaneous from the patient or generated by an artificial pace-maker.

At the moment when the contraction starts it will be adjustable after the ECG R wave. For this, the generator will have the capacity to detect the R wave either spontaneous from the patient or generated by the stimulus of a pace-maker.

The appearance of this electric activity will be what determines the start of the ring rotation for narrowing the module. It will be scheduled to start a short time after the QRS commencement to meet the physiologic period of isovolumetric contraction. After this time elapses, the rotation of the internal ring with toothed external profile will be started and with it the ventricular systolic emptying. With this, the possibility to produce asynchronic ventricular contractions with the spontaneous action of the patient is prevented.

The power supply preferred to feed said generator and driving member will be a large capacity battery allowing to implant it within the patient organism, periodically renewable, as it is presently done with the generators of the pace-makers. Said battery will offer the advantage not to rely on an external power supply which requires a connection between the outside and the inside of the organism.

With respect to above paragraph, it can be mentioned that, same as with the case of the pace-makers, as well said battery as the electronic generator will be installed at any point of the chest the location of which will be made suitable not to difficult further echocardiographic controls.

Alternatively and in the cases when the energetic requirement do not allow that the battery be internal, a transthoracic cable, known by itself but not illustrated, will connect the motor of the apparatus to the power supply, which can be external batteries (not shown) that the patient will carry in an haversack same as the bearers of an artificial heart.

Coming newly back to above mentioned parameters, the moment of contraction (A) must be determined by the appearance of the ventricular QRS complex which will be detected by means of a sensor similar to the one of a pace-maker.

If the patient bears a pace-maker, the spicula thereof will determine the start of the contraction in the beats induced by it.

There must be a delay between the moment QRS complex appears and the start of the contraction in order to meet the physiologic period of ventricular isovolumetric contraction also called the presphygmic period.

This time of delay will be adjustable and will be related to the cardiac frequency, so that higher is the heart rate and therefore shorter is the cycle length, shorter will be the delay corresponding to the time of isovolumetric contraction. Lower the cardiac frequency is, i.e., with longer cycle length, longer will be the presphygmic period.

As the volume to be expelled at each beat concretely depends on the diastolic time of the former cycle, the presphygmic period, i.e. the time elapsed between the detection of QRS and the start of the contraction will be adjusted according to the distance between the QRS of the beat to be regulated and the QRS of the former beat, which in electrocardiographic terms is expressed as the former R—R.

Scheduling said presphygmic period can be initially done according to the physiologic parameters depending on the heart rate and it must be possible to regulate it later on in each concrete patient, according to medical controls to be established to optimize each beat performance.

The duration of each contraction (B) which is known as "ejection period" also depends on the heart rate and is in inverted ratio from it, so that the higher the heart rate is and therefore shorter the cycle length, the shorter the ejection period is. With a lower heart rate, longer cycle length and longer ejection period.

As in the above chapter, the duration of the contraction will be initially scheduled according to general physiologic parameters depending on the former R—R interval to adjust the expulsion of each beat to the filling which occurred at the former diastole.

Same way, it must be possible to regulate it later on, depending on the evolution of each patient, to optimize the effectiveness of each beat.

At each beat, it must be possible to regulate the intensity of the contraction (C), i.e. the constriction the apparatus exerts on the cavities contained within it.

It must be possible to initially schedule this parameter according to the physician wish and the prior situation of each patient. It must also be possible to regulate it later on depending on the results obtained from each patient and the adjustments wished.

Maximum dilatation or distention will be determined in part since the beginning by the size of the apparatus placed to each patient.

In addition, at each case, the amplitude of the twist of the internal bag may be regulated to fit it. This way, for a larger return a larger cavity remains contained within it and higher will be the diastolic capacity. For a lower return lower will be the volume of the cavity and lower the diastolic filling.

Different sizes of apparatus will be provided depending on the size of the chest or heart of each patient as there exist different sizes of valvular prosthesis.

The size of the heart of the patient will be, surely, reduced in most cases because it will be one of the benefits to achieve and when it will be contained in the apparatus its diastolic and systolic diameters will be smaller.

As the initial size of the heart in most of the patients will be larger than normal, when inserting this apparatus in any of its variations, it will have sufficient room in the space previously occupied by the anomalously dilated heart and will not mean a shortage for the pulmonary expansion.

In addition to the performances of the described apparatus, stated at the beginning of this description, said apparatus provides following benefits:

it offers an atrial contraction similar to the physiologic one to patients who are in atrial fibrillation;

probably, some groups of patients will not require any more anticoagulation when they achieve rhythm and contractility in every cardiac cavity;

the improvement of the cardiac function may mean less requirement of drugs, a best state of health , improvement in the amount and quality of life and less requirement to be hospitalized.

What is claimed is:

1. Apparatus aiding the physiologic systolic and diastolic dynamics of cardiac cavities of a patient, said apparatus comprising:

a stable wrapping (12), acting as receptacle, having a contour similar to that of the ventricles (11, 11a) which it surrounds, the mouthpiece of which is attached to a first stiff ring (13) and with a distal tip (14) on which an apex (10) of the heart will be arranged, both said first stiff ring (13) and said tip (14) being fixed on the body skeleton of the patient;

a second stiff ring (18), having a slightly smaller diameter, coupled to said first stiff ring (13) which surrounds it, with possibility to revolvingly slide, supported guided on said first ring (13) and moving concentrically to it;

a bag (19) of flexible fabric, similar to the ventricle contour connected by its mouthpiece (19) to said second stiff ring (18), and a distal vertex (19b) of which is internally joined to said wrapping tip (14));

means for applying to said second stiff ring (18), during predetermined periods of time rotations to the right and to the left, having an adjustable amplitude, in synchronism with the ventricles (11, 11a) systolic and diastolic cycles determining a twist of the bag (19) which provokes a squeezing of the ventricles (11, 11a) contained within it, aiding so to the systolic emptying and later on , when rotating the ring (18) in an opposite direction, a relaxation which allows the diastolic filling; and control means to remote monitoring the application during the operating periods of time, of said rotations, in synchronism with the physiologic cardiac dynamics.

2. Apparatus, according to above claim characterized in that said wrapping (12) which is a stiff structure and said bag (19) of flexible fabric adopt an approximately conical shape.

3. Apparatus, according to claim 1, characterized in that it comprises a specific wrapping (12, 19) to be applied to the ventricles (11, 11a) and a wrapping designed to be applied to the atria (21, 21a) if required, so that the apparatus may be simple, solely ventricular, solely atrial or mixed ventricular and atrial.

4. Apparatus, according to the claim 1, characterized in that said means to apply rotations to the right and to the left to said stiff second ring comprise a driving member (27) the operation of which determines an alternate succession of spiral twists and expansions of said flexible bag (19) which surrounds the ventricular walls, fastened by its vertex (19b).

5. Apparatus, according to claim 4, characterized in that said driving member (27) is fastened by means of a support (28) to the first external ring (13) and its shaft possesses a pinion (29) which is geared with a peripheral toothed profile (30)of the external wall of the second internal ring (18) so that when said motor (27) acts, the ring (18) revolvingly moves, sliding conducted by a guiding configuration (31, 32) on the ring (13) which remains fixed.

6. Apparatus, according to the claim 3, characterized in that said wrapping applied to the atria (21, 21a) comprises a cap-like element (20) adapted to its contour and respecting the incuts (22) of caval and pulmonary veins (23) which converge in them, and means to squeeze said cap (20) and take it downward the ventricles (11, 11a) in an approximately cranio-caudal direction and thereafter to release it allowing the recovery-relaxation of said atrial cavities (21, 21a).

7. Apparatus according to claim 6, characterized in that said means to squeeze said cap (20) and then release it comprise tension members (24) having a toothed profile (24a) associated to toothed driving wheels (25) supported on the external wrapping (12) or on the external first ring (13) of the apparatus, said rotation of that wheels (25) driven by a motor (26) will make the atrial cap (20) go downward the ventricles (11, 11a) compressing the articles (21, 21a) obliging them to empty themselves and provoking the atria emptying through the mitral and tricuspid valves or to take them up and decompressing them, to allow the atrial diastole.

8. Apparatus according to the claim 6, characterized in that if the system is only an atrial system, a protecting sheath will wrap the ventricles (11, 11a) with the aim of preventing friction produced by the tension members (24) and to provide support to the driving system, the cap (20) of which being related by said tension members (24) at several points of its periphery.

9. Apparatus, according to claim 4 or 7, characterized in that the control means to monitor the apparatus comprise a small-sized electronic generator with an impulse transmitter of the type of a pace-marker, which can be scheduled, with possibility to generate two types of differentiated impulses and in that the driving motor (26, 27) is a compact, small-sized impulse motor with an activation electronic circuit so that according to the type of impulse received, it drives in rotation the shaft of said motor (26, 27) in one or the other direction.

10. Apparatus, according to claim 4 or 7, characterized in that the power supply of said driving member (26, 27) will be a large capacity and long lasting battery which may be implanted in the body of the patient.

11. Apparatus according to the claim 4 or 7, characterized in that the power supply is obtained from outside through a transthoracic cable which connects a motor (26, 27) and an activation circuit to an external generator and power supply, such as external batteries that the patient bears in an haversack.

12. Apparatus, according to claim 1, characterized in that it includes in addition means to keep fastened to the chest the first stiff external ring (13) of the assembly and the point (14) of the stiff wrapping (12) distal from it, so that said wrapping (12) is arranged around the heart (10) in order it cannot be taken away.

13. Apparatus, according to the claim 12, characterized in that said means consist in tension members (15–16) or semistiff members which relate the first ring (13) as well as the point (14) of the wrapping (12) to the ribs (17), adopting the required outline and adapting themselves to the anatomy of the region pass through suitable interstices in order to, without damaging nor compressing organic structures, be fastened to the ribs (17) in at least three differentiated areas.

14. Apparatus, according to the claim 12, characterized in that it comprises in addition ribbons or strips which surround the heart (10) extending on said stiff wrapping (12) and keeping it in operative position, and being said ribbons fastened by means of a junction to each other or to the external part of the stiff wrapping (12) by stitching or another fastening means.

15. Apparatus, according to the claim 1, characterized in that in the event it is a ventricular and atrial mixed system, the fastening means of the wrapping or cap (20) of the atria (21, 21a) extend on the wrapping (12) of the ventricles (11, 11a).

16. Apparatus, according the claim 1, characterized in that the structure, surface and distribution of the fibres of said bag will be selected so that they may be twisted, applying different pressures on one and the other ventricles (11, 11a).

* * * * *